United States Patent
Sydney et al.

(10) Patent No.: US 6,458,138 B1
(45) Date of Patent: *Oct. 1, 2002

(54) SELECTIVE COATING OF A BALLOON CATHETER WITH LUBRICIOUS MATERIAL FOR STENT DEPLOYMENT

(75) Inventors: Gregory T. Sydney, Sharon, MA (US); Russ Seiber, Southboro, MA (US); Arthur R. Madenjian, Winchester, MA (US); Annette Belovi, Watertown, MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/971,435

(22) Filed: Oct. 4, 2001

(Under 37 CFR 1.47)

Related U.S. Application Data

(63) Continuation of application No. 08/740,727, filed on Nov. 1, 1996, now Pat. No. 6,306,144, which is a continuation-in-part of application No. 08/409,797, filed on Mar. 24, 1995.

(51) Int. Cl.[7] .............................................. A61F 11/00
(52) U.S. Cl. .................... 606/108; 604/96.01; 604/265; 606/194; 623/1.11
(58) Field of Search .............................. 604/265, 96.01; 606/192–194, 108; 623/1.1, 1.11, 1.12

(56) References Cited

U.S. PATENT DOCUMENTS

| | | | |
|---|---|---|---|
| 2,921,981 A | 1/1960 | Keough | 128/349 |
| 2,927,584 A | 3/1960 | Wallace | 128/349 |
| 3,664,328 A | 5/1972 | Moyle, Jr. | 128/2 |
| 3,967,728 A | 7/1976 | Gordon et al. | 206/364 |
| 4,026,296 A | 5/1977 | Stoy et al. | 128/349 |
| 4,465,072 A | 8/1984 | Taheri | 128/348.1 |
| 4,636,346 A | 1/1987 | Gold et al. | 264/139 |
| 4,889,744 A | 12/1989 | Quaid | 427/2 |
| 4,921,483 A | 5/1990 | Wijay et al. | 604/96 |
| 4,952,357 A | 8/1990 | Euteneuer | 264/129 |
| 5,032,113 A | 7/1991 | Burns | 604/96 |
| 5,041,100 A | 8/1991 | Rowland et al. | 604/265 |
| 5,074,845 A | 12/1991 | Miraki et al. | 604/101 |
| 5,100,381 A | 3/1992 | Burns | 604/96 |
| 5,100,429 A * | 3/1992 | Sinofsky et al. | |
| 5,108,416 A | 4/1992 | Ryan et al. | 606/194 |
| 5,120,322 A | 6/1992 | Davis et al. | 604/265 |
| 5,135,474 A | 8/1992 | Swan et al. | 604/98 |
| 5,135,487 A | 8/1992 | Morrill et al. | 604/96 |
| 5,135,516 A | 8/1992 | Sahatjian et al. | 604/265 |
| 5,209,730 A | 5/1993 | Sullivan | 604/96 |
| 5,229,211 A | 7/1993 | Murayama et al. | 428/424 |
| 5,232,444 A | 8/1993 | Just et al. | 604/96 |
| 5,503,631 A | 4/1996 | Onishi et al. | 604/96 |
| 5,571,166 A * | 11/1996 | Dinh et al. | |
| 5,624,450 A * | 4/1997 | Glastra | |
| 5,643,278 A * | 7/1997 | Wijay | |
| 5,746,745 A | 5/1998 | Abele et al. | |
| 5,766,201 A * | 6/1998 | Ravenscroft et al. | |
| 5,830,217 A * | 11/1998 | Ryган | |
| 5,913,871 A * | 6/1999 | Werneth et al. | |
| 6,306,144 B1 * | 10/2001 | Sydney et al. | |

FOREIGN PATENT DOCUMENTS

| | | |
|---|---|---|
| DE | 3519626 | 5/1995 |
| EP | 0 380 102 A1 | 8/1990 |
| WO | WO 91/08790 | 6/1991 |
| WO | WO 94/07561 | 4/1994 |

OTHER PUBLICATIONS

U.S. application Ser. No. 08/409,797, filed Mar. 24, 1995, Sidney et al.

U.S. application Ser. No. 08/740,727, filed Nov. 1, 1996.

* cited by examiner

*Primary Examiner*—Mark Backelman
(74) *Attorney, Agent, or Firm*—Vidas, Arrett & Steinkraus, P.A.

(57) ABSTRACT

A predetermined arrangement of differentially lubricious areas on a balloon catheter for controlling against unexpected movement of a stent carried thereon when in situ in the body.

20 Claims, 1 Drawing Sheet

SELECTIVE COATING OF A BALLOON CATHETER WITH LUBRICIOUS MATERIAL FOR STENT DEPLOYMENT

RELATIONSHIP TO OTHER APPLICATION

This application is a continuation of Ser. No. 08/740,727 filed Nov. 1, 1996, now U.S. Pat. No. 6,306,144, which is a continuation-in-part of co-pending U.S. patent application Ser. No. 08/409,797, filed Mar. 24, 1995, which is herein incorporated by reference.

FIELD OF THE INVENTION

The invention pertains to the manufacture of a stent carrying balloon catheter having a predetermined arrangement of differentially lubricious areas on the balloon catheter to prevent unexpected movement of the stent when in situ in the body and to insure precise stent deployment.

BACKGROUND OF THE INVENTION

This invention relates to stent carrying balloon catheters, sometimes referred to as dilatation catheters, for use in angioplasty and other various vessel repair procedures. Angioplasty has become recognized as an efficient and effective method of opening stenoses in the vascular system. In the most widely used form of angioplasty, a balloon catheter is guided through the vascular system until the balloon, which is carried at the distal end of a catheter shaft, and which may carry an expandable stent, is positioned across the stenosis or lesion, i.e., vessel obstruction. The balloon is then inflated to apply pressure to the obstruction which is essentially remolded by pressing it against the inner wall of the vessel whereby the vessel is opened for improved flow. Due the expansion of the balloon, the stent, which is situated on the balloon, is also expanded and released to aid in support and/or repair of the vessel wall.

Balloon catheters are of various types. One type is fed over a guide wire (i.e., "over-the-wire" catheters) and another type serves as its own guide wire (i.e., "fixed-wire" catheters). Variations of these two basic types also have been developed such as the so called "rapid exchange" type, "innerless" catheters, and others. As used herein, the term "balloon catheter" is meant to include all of the various types of angioplasty catheters which carry a balloon for performing angioplasty and any other type of stent carrying balloon catheter. Balloon catheters may also be of a wide variety of inner structure, such as different lumen design, of which there are at least three basic types: triple lumen, dual lumen and co-axial lumen. All varieties of internal structure and design variation are meant to be included by use of the term "balloon catheter" herein.

When used in percutaneous transluminal coronary angioplasty (PTCA), the balloon catheter is typically advanced through a guide catheter to a preselected vessel location, such as the aorta, for example. Using fluoroscopy, the surgeon manipulates the catheter until the balloon is located across the stenosis or obstruction. As already pointed out, this may involve the use of a guide wire over which the catheter is moved or alternatively the catheter may act as its own guide wire, depending on the particular design. The manipulation of the stent carrying balloon catheter through the guide catheter and through the vessels to the obstruction requires the balloon catheter to have a number of different features.

One such feature is the use of a lubricious coating over the exterior surfaces of the catheter and balloon to facilitate movement of the catheter through the sometimes tortuous paths within the vascular system to the preselected vessel location for performing the angioplasty. A wide variety of such lubricious coatings have become commonplace for use with respect to catheters and other devices which are insertable into the body in connection with surgical procedures and the like. All such coatings are intended to be included herein with respect to the use of the term "lubricious coating". Examples of such coatings include silicone and most preferably hydrophilic coatings involving hydrogel polymers or the like, such as polymer networks of a vinyl polymer and an uncrosslinked hydrogel, for example. Polyethylene oxide (PEO) is a preferred hydrogel. A preferred vinyl polymer is neopentyl glycol diacrylate (NPG). Such compositions are more fully disclosed in co-pending U.S. patent application, Ser. No. 07/809,889 which is assigned to the same assignee as is the present invention and which is incorporated herein by reference.

These coatings have even been known to include certain agents such as drugs which may be permanently entrapped in the coating or leachable therefrom into the body. For example, heparin has been used in such a fashion. Heparin is well known as an agent which is often used to inhibit clot formation in the blood. Again, the term "lubricious coating" is meant to include all such variations.

One problem with a stent carrying balloon catheter having a lubricious coating is that during location and release of the carried stent, the stent tends to slip off the balloon due to the lubricious coating on the balloon. Coating both the shaft and balloon of the catheter inhibits the doctor's ability to locate, activate and deploy stents at any particular lesion. The stent is sometimes worked off the balloon portion during the insertion of the catheter and during the expansion of the balloon. This unexpected movement of the stent might be regarded negatively by a surgeon. The present invention provides for more secure connection between the balloon and the stent to prevent such slippage. Thus, though high lubricity is desirable for general movement, it is also desirable to provide a means of anchoring or positioning the stent in a fixed location on the balloon so as to avoid unexpected movement thereof upon the balloon during positioning and expansion.

SUMMARY OF THE INVENTION

The invention is a stent delivery catheter which has a lubricious coating on the shaft and, either, partial or no lubricious coating or an adhesive coating, or a combination thereof on the balloon. The lubricious coating, which is preferably hydrophilic, provides lubricity to the catheter while the uncoated or partially coated or adhesive coated balloon is able to retain the stent during positioning and release without concern for coating induced slippage. This is accomplished by the present invention through the selective arrangement of lubricious and/or adhesive coatings on the balloon catheter in which at least a portion of the balloon body is uncoated or less slippery or tacky while a relatively more lubricious coating is placed on at least a substantial portion of the catheter shaft extending in a proximal direction from the balloon toward the proximal end of the catheter shaft.

Generally then, the invention contemplates an improvement in the arrangement of lubricious coating(s) and/or adhesive coating(s) on the catheter to avoid stent slippage and to better anchor the stent in position for performing angioplasty or other vessel repair. This is accomplished by what may be termed herein as "differential coating" or "selective lubricating". By this is meant that the lubricious properties of the catheter are selectively designed or constructed and arranged in a predetermined manner such that the catheter shaft i.e, substantially all of the catheter generally exhibits more lubricity than the balloon generally. In short, the catheter is more slippery than the balloon, relatively speaking. It can be seen that an important feature of the invention lies in the uncoated or less slippery balloon or portion thereof relative to the rest of the catheter so that the stent is more controllable.

Such an arrangement may be accomplished in a number of different ways. For example, in one embodiment, a lubricious coating may be provided over substantially the entire catheter, except for the balloon per se. In this embodiment, the balloon does not include any lubricious coating at all. The stent, which is placed over the balloon, is therefore not susceptible to slippage due to the greater coefficient of friction than a balloon with lubricant might have.

The balloon also may be coated partially or with a less lubricious or less slippery coating than the coating covering the shaft of the catheter. In such an instance, two different coatings may be used, such as a PEO composition as aforementioned on the catheter shaft and so forth, while a silicone coating is placed on the balloon per se. The balloon may also have specific areas coated, while leaving others uncovered to provide suitable contact with the stent.

In another variation, different compositions of PEO may be used on the shaft and balloon. In the PEO compositions aforementioned, comprised of PEO and NPG in isopropyl alcohol and water, variations in the amount of PEO content affect the final lubricity of the composition; the higher the percentage PEO, the higher the lubricity. Therefore, one may utilize a relatively higher percentage PEO composition on a catheter shaft and a relatively low percentage composition on the balloon to achieve the ends of this invention also i.e., "differential" or "selective" lubricity over a catheter. Of course, other compositions may also be utilized in this way.

Another embodiment comprises a coated catheter shaft, coated balloon cones and a coating on at least the distal waist of the balloon extending to the distal catheter tip, the balance of the balloon body having no coating or one of less lubricity.

In an additional embodiment, both the proximal and distal balloon cones are so coated similarly to the catheter shaft or at least the distal cone. In accordance with the invention, the balance of the balloon body is uncoated or coated with a relatively less lubricious coating.

In still a further embodiment, the balloon is partially or entirely coated with a tacky adhesive.

The advantage of the present invention is the ability to have a coated catheter which offers ease of movement through the vasculature along with the ability to effectively engage and deploy stents at any particular lesion without slippage or premature activation.

BRIEF DESCRIPTION OF THE DRAWINGS

A detailed description of the invention is hereafter described with specific reference being made to the drawings in which.

DETAILED DESCRIPTION OF THE INVENTION

Figure 1:
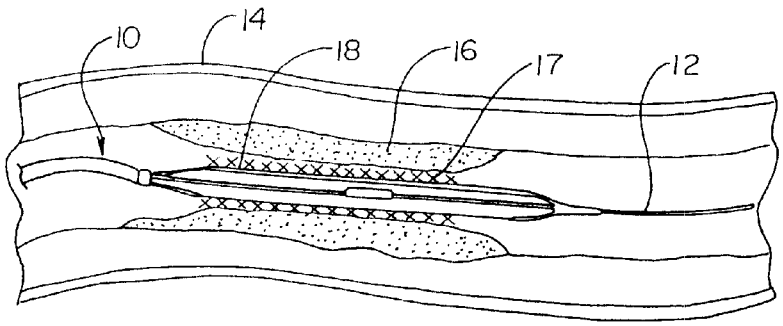
FIG. 1 is a diagrammatic showing of a balloon catheter in which the balloon is positioned across an obstruction in a vessel prior to inflation and an expandable stent is positioned over the balloon.
Figure 2:
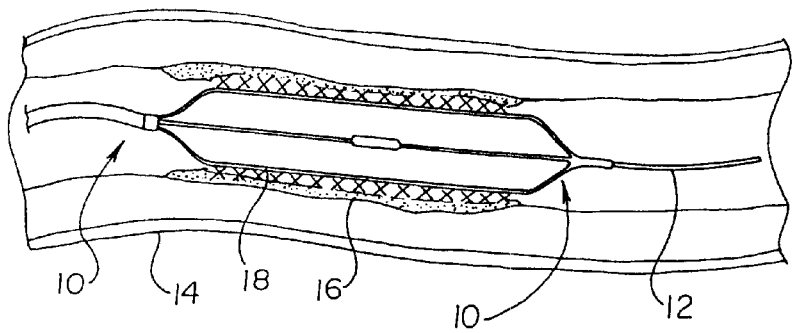
FIG. 2 is a diagrammatic showing of the positioned balloon catheter of FIG. 1 with the balloon inflated against the obstruction and the stent expanded.

FIGS. 1 and 2 show a stent carrying balloon catheter, generally indicated at 10, of the over-the-wire type having a guide wire 12 over which the catheter has been moved within a vessel 14 to the location of an obstruction 16. As can be seen in the Figures, balloon 18 and stent 17 are positioned across obstruction 16 while the balloon 18 is uninflated (shown in FIG. 1). Upon inflation (shown in FIG. 2), as the balloon expands and exerts pressure against stent 17 and obstruction 16, it is possible for the stent to slip out of place, either forward or backward along the balloon, if care is not taken to make sure the catheter is in a fixed position. As shown in FIG. 2, if the catheter is held in a fixed position, the expanding balloon expands the stent 17 and presses against obstruction 16 molding it against the inner walls of vessel 14 to open the vessel. This method is also used for a collapsed or damaged vessel. In such a case, the expanded stent supports the vessel wall and/or repairs damaged tissue. As already indicated with respect to the present invention, the surface of balloon 18 shown contacting stent 17 is best not coated, or coated with a less lubricious coating than the catheter proper, or coated with an adhesive, in order to provide an "anchoring" effect so that the balloon engages the stent. This is more fully described hereinbelow with reference to FIGS. 3 and 4.

By "anchoring" the stent 17 to the balloon 18 according to the invention, the stent 17 is also prevented from slipping off during the navigation of the balloon through the body to the targeted area. Prior to the present invention, when the balloon was coated with a lubricious coating along with the majority of the rest of the catheter, the loaded stent had a tendency to slip off the balloon or be shifted out of place. This effect is due to the vessel wall and other obstructions which act as a drag on the carried stent as it is transported to the targeted area. The present invention remedies this problem.

Figure 3:
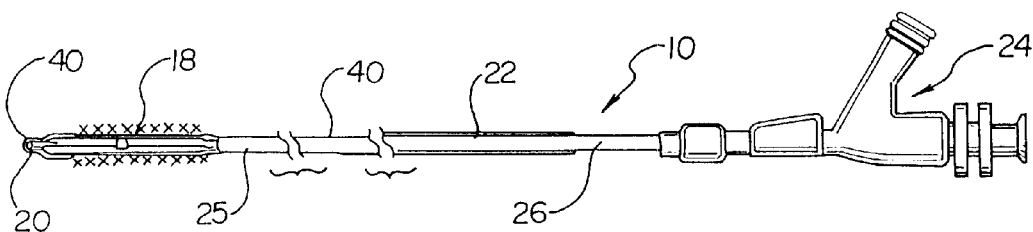
FIG. 3 is a schematic showing of a typical balloon catheter, having a stent loaded thereon.

FIG. 3 shows a typical stent carrying balloon catheter which may incorporate any of the various aforementioned design variations for catheters. For purposes of understanding the present invention it is only important to note that catheter 10 includes a balloon generally indicated at 18, a stent 17, a distal tip 20, a shaft 22 and a manifold portion generally indicated at 24. Shaft 22 is comprised of a proximal end portion 26 and a distal end portion 25 where it joins balloon 18. Shaft 22 preferably is made from Nylon- 11 and low and high density polyethylene.

Figure 4:
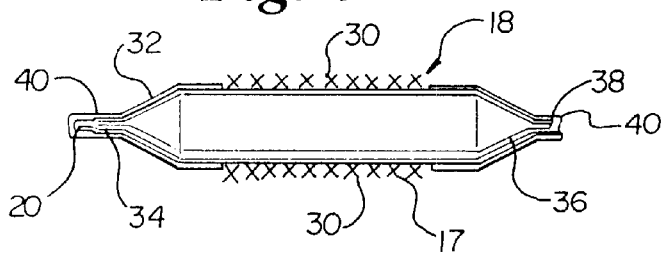
FIG. 4 is a schematic diagram showing the basic anatomy of a catheter balloon coated according to one preferred embodiment of the invention and a stent loaded thereon.

As can be seen in FIG. 4, balloon 18 includes a body portion 30, a proximal cone portion 36, a proximal waist portion 38, a distal cone portion 32 along with a distal waist portion 34 and a stent 17 loaded thereon.

In accordance with one embodiment of the selective arrangement of the lubricious coatings on the catheter as contemplated herein, such a coating is shown at 40 extending over proximal cone 36 (optional), in a proximal direction over shaft 22 toward the proximal end portion 26 thereof to thereby cover a substantial portion of shaft 22. Coating 40 is also optionally included on the distal cone 32, distal waist portion 34 and the distal tip of the catheter 20 as can be seen best in FIG. 4. The balance 30 of the balloon is either uncoated or coated with a less lubricious composition or coated with an adhesive. The absence of a lubricious coating on the balloon allows the stent 17 to remain more firmly in contact with the balloon itself. The balloon may be partially covered with lubricious material as long as a portion of the balloon is uncoated, or coated with a less lubricious material, in order to firmly hold the stent in place.

As is known in the art with respect to balloon catheters and lubricious coatings, the coating will be relatively thin and preferably bonded to the catheter body surfaces, although not necessarily. Silicone is an example of an unbonded lubricant. The PEO based coating cited earlier is an example of a bonded one. In the Figures, the relative thickness of coating is greatly exaggerated for clarity. However, in accordance with standard practices in the art, such coatings may nominally be of a thickness on the order of 20–50 um or less and will be applied in a variety of ways depending on the type of coating involved and the particular selective arrangement of the coating desired. For example, in the case of various polymeric hydrophilic coatings it has been found convenient to utilize an elastic mask to block the body portion of the balloon from being coated with the slippery hydrophilic coating. The mask, in a preferred form, is a heat shrink polyolefin sized to provide a slight interference fit around the balloon to keep the mask in place during processing. In one preferred form, the uncoated length of the area masked has been about ⅝" of an inch centered on the body portion of the balloon and extending around its peripheral surface. Such an arrangement is indicated in FIG. 4. Of course, at least some of body of the balloon is left uncoated as well or coated with a relatively less lubricious coating than the balance of the catheter proper. Preferably, the entire balloon portion which is in contact with the stent is left uncoated.

Upon completion of the polymer coating procedure, the mask is then removed to expose the uncoated balloon body portion. In such an arrangement, the shaft and balloon cones and waists, being unmasked during the coating procedure, are coated with the same slippery coating as is placed on the rest of the catheter. As is already known, such coatings are typically applied to the catheter surfaces in the form of a solution which is allowed to dry and is subsequently cured usually by heat or Ultraviolet light for a short period of time.

Other means for achieving the selective placement of coating(s) on the catheter may include the use of a release agent such as an oil which may be spread over the area which it is desired will remain uncoated. After curing of the coating, this area is then exposed by simply peeling the coating off the area carrying the oil. Also, if desired, one may rinse or wipe a portion of the coating off the balloon before the coating is cured. Another alternative is to modify the coating in the area of the balloon which is to remain uncoated such as using an ultraviolet blocker.

A final selective coating arrangement according to the invention may also be made by first coating with a less slippery, compatible coating over the balloon and possibly more of the catheter, then masking, applying highly slippery coatings as desired and proceeding as normal or vice versa.

This invention is equally applicable to balloons of the compliant type and to those of the non-compliant type. A wide variety for the materials of the balloons is well known, some examples of which, to name a few, include ethylene vinylacetate copolymer polyethylene terephthalate, polyethylene, polyolefin copolymer and high density polyethylene.

Masking materials are most conveniently heat shrink polyethylene on mandrels of sizes appropriate to the particular balloon and are placed thereon. The coating may comprise a mix of a higher molecular weight soluble polymer such as PEO and a UV curable diacrylate in isopropyl alcohol and water containing a trace of photoinitiator. The coating solution is wiped onto selected areas of the catheter device which is then passed to a UV chamber, purged of oxygen, exposed to UV and then removed. The mask is removed, the area is cleaned ultrasonically with a water bath to remove any drips. The uncoated portion of the balloon is left as is or a less lubricious coating is applied to it such as silicone or a polymer coating with a lesser percentage of hydrogel content. Other methods of application will be known to those familiar with the art.

In a further embodiment of the invention the balloon exhibits different frictional characteristics in its inflated and non-inflated states. The balloon catheter has a low coefficient of sliding friction in a deflated state and a higher coefficient of friction in a inflated state. The balloon has a high coefficient of sliding friction in a deflated state for facilitating the transport of a contracted stent and a lower coefficient of friction in an inflated or expanded state. Further disclosure of such balloon surface and material characteristics can be found in U.S. patent application Ser. No. 08/609,274, filed on Mar. 1, 1996, which is incorporated herein by reference.

In accordance with one aspect of this invention a medical balloon is formed of a thin material for expansion from a compact state to an expanded state in a patient's vessel. The balloon is formed with a first material portion or spaced first material portions such that the balloon in its compact state essentially exposes the exterior surfaces of only the first material portion or portions. In the expanded state the balloon exposes the exterior surfaces of both the first and remaining material portions for contact with surrounding vessels. The exterior surface on a first material portion has an integral surface with a coefficient of friction that differs from the coefficient of friction of the exterior surface of a remaining portion of the balloon.

In accordance with another aspect of the referenced invention a stent delivery system includes a catheter with an inflation lumen, and a medical balloon formed of a thin material positioned at the distal end of the catheter in communication with the inflation balloon so the balloon is expansible from a compact state to an expanded state in response to the injection of an inflation fluid through the inflation lumen. A first material portion or a plurality of first spaced material portions are located so that the balloon essentially exposes the exterior surfaces of only the first material portion or portions in its compact state. As the balloon expands, it expands the stent and exposes the exterior surfaces of the first material portion and of the remaining material portion. The exterior surface of a first material portion has a coefficient of friction that is greater than the coefficient of friction of the exterior surface of the remaining portion of the balloon, such that the balloon in its compact state engages and provides friction to hold the stent in place on the balloon and in its expanded state facilitates the release of the balloon from the stent.

In a further embodiment of the present inventive concept, the balloon itself may be coated either partially or completely, but at least in areas in which a loaded stent would have contact with, with a tacky composition which aids in retaining a loaded stent in place during the tortuous location of the stent at a target position of a vessel. The balloon is coated with an adhesive, such as an elastomeric based adhesive, i.e. polyisobutylene, and pressure sensitive-type adhesives, i.e. polyamides and polyacrylate, making the surface of the balloon which would be in contact with a loaded stent tacky. The bond which is created between the coated balloon and loaded stent is only strong enough to prevent slippage of the stent, but is weak enough to release when the balloon is expanded. The portions of the balloon which are coated and the tackiness of the adhesive may vary to achieve this result. One such pattern involves coating longitudinal strips along the balloon which are accessible for engagement while the balloon is deflated. A similar pattern can be seen in U.S. patent application Ser. No. 08/609,274, as discussed above. With such a pattern, it is contemplated that the exposed surface area when the balloon is collapsed would be coated with adhesive to achieve a selective tacky coating on the balloon. Preferably, the balloon is coated by a tacky coating or a coating with a high coefficient of friction, i.e. a static coefficient of friction of about 0.2–0.4. The coating utilized to coat the balloon should be of higher coefficient of friction than the coating used to coat the shaft.

Preferably, the adhesive used is a aqueous dispersion of ethylene vinyl acetate (EVA) or a water-based dispersion based on high-molecular weight ethylene interpolymers, such as ADCOTE® 37P147, which is manufactured by Morton®. The major use for Adcote 37P147 is as an in-line laminating adhesive, a primer, or as a base for compounding coatings and adhesives. Adcote 37P147 is suggested for applications which require the property of low temperature heat activation and hot tack. This product exhibits good adhesion to Mylar, polyethylene, polypropylene, aluminum foil and PVDC coated glassine. For surface coating, Adcote 37P147 must be compounded. Typical Dispersion Properties are: Solids—45%; Viscosity—500 cps; pH—10; and Weigh/Gallon —8.2 lbs. The dispersion is stable in most alkaline systems, but may coagulate under acidic conditions. Adcote 37P147 exhibits good storage stability, but mixing just prior to use is recommended in order to assure product uniformity. Freezing conditions should be avoided as freezing will coagulate the dispersion. Standard coating techniques, such as wire-wound rods and gravure, can be employed. However, as these dispersions are water-based, care should be taken to minimize the generation of foam. If a tendency to foam occurs, the addition of 0.05–0.2% (based on wet dispersion weight) of Foamkill 614 (Crucible Chemical Company, Donaldson Center, Greenville, SC 29605) or Adcote 7R1 is recommended. The dispersion may be reduced with water, preferably slightly basic (buffer solution of about ph 10), if a large amount is to be added. Drying should be effected by heat giving rise to an approximate surface web temperature of 150–180° F. Coating weights for adhesive use of 1.0–2.0 lbs/ream is adequate for most applications.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

This completes the description of the preferred and alternate embodiments of the invention. Those skilled in the art may recognize other equivalents to the specific embodiment described herein which equivalents are intended to be encompassed by the claims attached hereto.

What is claimed is:

1. A balloon catheter having a shaft and a balloon associated therewith, the balloon having a proximal end portion, a distal end portion and a central portion, wherein the balloon has a collapsed state in which a surface portion of the central portion is exposed and an expanded state, the balloon catheter further comprising a first lubricious coating on a portion of the shaft and a second coating on at least a portion of the exposed surface of the balloon when the balloon is in its collapsed state, wherein the second coating comprises an adhesive and wherein both ends of the balloon are coated with the first lubricious coating.

2. The catheter according to the claim 1, wherein at least a portion of the balloon is uncoated, as defined by the balloon material forming the outer surface thereof.

3. The catheter according to claim 1 wherein the central portion of the balloon is substantially coated with the second coating.

4. The catheter according to claim 1, wherein the entire balloon is coated with the first lubricious coating and at least a portion of the central portion is further coated with the second coating.

5. The catheter according to claim 1, wherein the first lubricious coating comprises a polyethylene oxide composition.

6. The catheter according to claim 1, wherein the first coating further comprises silicone.

7. The catheter according to claim 1, wherein the second coating is only on the central portion of the balloon.

8. The catheter according to claim 1, wherein the first lubricious coating comprises a hydrophilic coating.

9. The catheter according to claim 1, further comprising a stent positioning on the balloon and the adhesive.

10. The catheter according to claim 1, further comprising a distal tip portion, wherein the distal tip is similarly coated as the shaft.

11. The catheter according to claim 1, wherein the entire balloon body is coated with the second coating.

12. The catheter according to claim 1, wherein only the central portion of the balloon body is coated with the second coating.

13. The catheter according to claim 1, wherein the second coating has a higher coefficient of friction than the first lubricious coating.

14. The catheter according to claim 13, wherein the second coating has a static coefficient of friction of about 0.2–0.4.

15. The catheter according to claim 1, wherein the second coating comprises a water-based dispersion based on high-molecular,weight ethylene interpolymers.

16. The catheter according to claim 1, wherein the second coating comprises an aqueous dispersion of ethylene vinyl acetate.

17. The catheter according to claim 1, wherein the entire central portion of the balloon is coated with the second coating, wherein the second coating has a static coefficient of friction of about 0.2–0.4.

18. The catheter according to claim 1, wherein the adhesive is an elastomeric based adhesive or a pressure sensitive-type adhesive.

19. The catheter according to claim 1, wherein the adhesive is chosen from the group consisting of polyisobutylene, polyamides and polyacrylate.

20. The catheter according to claim 1, wherein the adhesive is tacky.

* * * * *

UNITED STATES PATENT AND TRADEMARK OFFICE
CERTIFICATE OF CORRECTION

PATENT NO.    : 6,458,138 B1
DATED         : October 1, 2002
INVENTOR(S)   : Gregory Sidney et al.

It is certified that error appears in the above-identified patent and that said Letters Patent is hereby corrected as shown below:

<u>Title page,</u>
Item [63], delete "...which is a continuation-in-part of application No. 08/409,797, filed on Mar. 24, 1995."

Signed and Sealed this

Seventeenth Day of June, 2003

JAMES E. ROGAN
*Director of the United States Patent and Trademark Office*